(12) United States Patent
Lemonis et al.

(10) Patent No.: US 10,736,781 B2
(45) Date of Patent: Aug. 11, 2020

(54) ADJUSTING LASER ENERGY IN ACCORDANCE WITH OPTICAL DENSITY

(75) Inventors: Sissimos Lemonis, Schwaig (DE); Stefan Wendl, Schwaig (DE)

(73) Assignee: Alcon Inc. (CH)

( * ) Notice: Subject to any disclaimer, the term of this patent is extended or adjusted under 35 U.S.C. 154(b) by 1086 days.

(21) Appl. No.: 14/370,901

(22) PCT Filed: Jan. 18, 2012

(86) PCT No.: PCT/EP2012/000224
§ 371 (c)(1),
(2), (4) Date: Jul. 7, 2014

(87) PCT Pub. No.: WO2013/107468
PCT Pub. Date: Jul. 25, 2013

(65) Prior Publication Data
US 2015/0202085 A1 Jul. 23, 2015

(51) Int. Cl.
*A61F 9/008* (2006.01)
(52) U.S. Cl.
CPC ...... *A61F 9/00827* (2013.01); *A61F 9/00825* (2013.01); *A61F 9/00831* (2013.01); *A61F 9/00836* (2013.01); *A61F 2009/0087* (2013.01); *A61F 2009/00844* (2013.01); *A61F 2009/00855* (2013.01); *A61F 2009/00872* (2013.01)
(58) Field of Classification Search
CPC .............. A61F 9/00877; A61F 9/00825; A61F 9/00831; A61F 9/00836; A61F 2009/00844; A61F 2009/00855; A61F 2009/0087; A61F 2009/00872

USPC ............................................................ 606/4
See application file for complete search history.

(56) References Cited

U.S. PATENT DOCUMENTS

| | | | |
|---|---|---|---|
| 6,099,521 A | 8/2000 | Shadduck | |
| 7,584,756 B2 | 9/2009 | Zadoyan et al. | |
| 2004/0243111 A1 | 12/2004 | Bendett et al. | |
| 2005/0203494 A1* | 9/2005 | Holliday | A61F 9/008 606/5 |
| 2007/0173796 A1 | 7/2007 | Kessler et al. | |
| 2009/0126870 A1 | 5/2009 | Zadoyan et al. | |
| 2009/0171329 A1 | 7/2009 | Raksi et al. | |
| 2009/0299347 A1* | 12/2009 | Vogler | A61F 9/008 606/5 |
| 2009/0326650 A1 | 12/2009 | Zickler et al. | |
| 2010/0324542 A1 | 12/2010 | Kurtz | |
| 2011/0022037 A1 | 1/2011 | Bille et al. | |

(Continued)

FOREIGN PATENT DOCUMENTS

| | | |
|---|---|---|
| CN | 101896144 A | 11/2010 |
| CN | 102026601 A | 4/2011 |

(Continued)

*Primary Examiner* — Aaron F Roane
(74) *Attorney, Agent, or Firm* — Kenneth Bassinger, Esq.

(57) ABSTRACT

In certain embodiments, a device comprises a laser device and a control computer. The laser device directs a laser beam with laser energy through an outer portion of an eye to a target portion of the eye. The control computer receives an optical density measurement of the outer portion, determines the laser energy according to the optical density measurement, and instructs the laser device to direct the laser beam with the laser energy through the outer portion of the eye to the target portion of the eye.

6 Claims, 8 Drawing Sheets

(56) References Cited

U.S. PATENT DOCUMENTS

| | | |
|---|---|---|
| 2011/0040293 A1 | 2/2011 | Bor |
| 2011/0160711 A1* | 6/2011 | Naranjo-Tackman ........................ A61F 9/00825 606/6 |
| 2011/0282333 A1* | 11/2011 | Herekar .............. A61F 9/00821 606/5 |

FOREIGN PATENT DOCUMENTS

| | | |
|---|---|---|
| CN | 102137732 | 7/2011 |
| DE | 102005046130 A1 | 3/2007 |
| DE | 102010022634 A1 | 12/2011 |
| EP | 0903133 A2 | 3/1999 |
| EP | 2352210 A1 | 3/2011 |
| JP | 2003092566 A2 | 3/2003 |
| JP | 2007-527731 A | 10/2007 |
| JP | 2008-029833 A | 2/2008 |
| JP | 2009-502289 A | 1/2009 |
| JP | 2016-005817 A | 1/2016 |
| WO | 2011038935 | 4/2001 |
| WO | 2003/092566 | 11/2003 |
| WO | 2005007002 A1 | 1/2005 |
| WO | 2006023535 A2 | 3/2006 |
| WO | 2010075571 A2 | 7/2010 |

\* cited by examiner

ADJUSTING LASER ENERGY IN ACCORDANCE WITH OPTICAL DENSITY

CROSS REFERENCE TO RELATED APPLICATIONS

This application is a section 371 national stage phase of International Application No. PCT/EP2012/000224, filed 18 Jan. 2012, titled "ADJUSTING LASER ENERGY IN ACCORDANCE WITH OPTICAL DENSITY," which is hereby incorporated by reference in its entirety.

TECHNICAL FIELD

The present disclosure relates generally to surgical systems, and more particularly to adjusting laser energy in accordance with optical density.

BACKGROUND

The cornea is normally a clear outer layer of the eye. Cloudiness of the cornea is a loss of transparency of all or a portion of the cornea. The cloudiness may be caused by any of a number of conditions, such as chemical burns, surgery, trauma, poor nutrition, or disease. The cloudiness reduces the amount of light entering the eye, which may impair vision.

BRIEF SUMMARY

In certain embodiments, a device comprises a laser device and a control computer. The laser device directs a laser beam having laser energy through an outer portion of an eye towards a target portion of the eye. The control computer receives an optical density measurement of the outer portion, determines the laser energy according to the optical density measurement, and instructs the laser device to direct the laser beam with the laser energy through the outer portion of the eye towards the target portion of the eye.

In certain embodiments, a method includes receiving, at a control computer, an optical density measurement of an outer portion of an eye. Laser energy of a laser beam is determined by the control computer according to the optical density measurement. A laser device is instructed by the control computer to direct the laser beam with the laser energy through the outer portion of the eye towards a target portion of the eye.

In certain embodiments, a device comprises a laser device and a control computer. The laser device directs a laser beam with laser energy towards a target portion of an eye. The control computer instructs the laser device to direct trial shots towards a trial portion, establishes effects of the trial shots on the trial portion, determines the laser energy according to the effects, and instructs the laser device to direct the laser beam with the laser energy towards the target portion of the eye.

In certain embodiments, a method comprises instructing a laser device to direct trial shots towards a trial portion, establishing effects of the trial shots on the trial portion, determining the laser energy according to the effects, and instructing a laser device to direct a laser beam with the laser energy towards a target portion of the eye.

BRIEF DESCRIPTION OF THE DRAWINGS

Exemplary embodiments of the present disclosure will now be described by way of example in greater detail with reference to the attached figures, in which:

FIGS. 3A through 4D illustrate examples of directing trial shots at a patient cornea according to certain embodiments;

DESCRIPTION OF EXAMPLE EMBODIMENTS

Referring now to the description and drawings, example embodiments of the disclosed apparatuses, systems, and methods are shown in detail. The description and drawings are not intended to be exhaustive or otherwise limit or restrict the claims to the specific embodiments shown in the drawings and disclosed in the description. Although the drawings represent possible embodiments, the drawings are not necessarily to scale and certain features may be exaggerated, removed, or partially sectioned to better illustrate the embodiments.

Figure 1A:
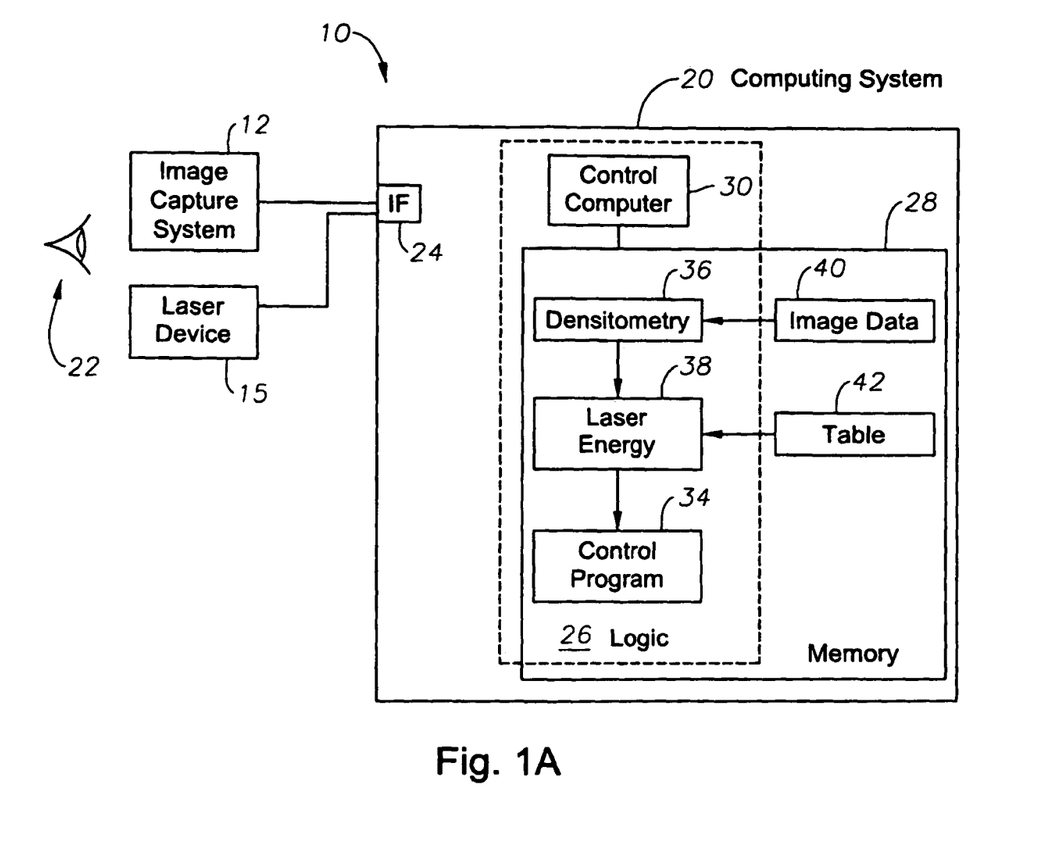
FIG. 1A illustrates an example of a system that can adjust laser energy according to optical density values in certain embodiments.

FIG. 1A illustrates an example of a system 10 that can adjust laser energy according to optical density values in certain embodiments. In certain embodiments, the system 10 can receive an optical density measurement of the outer portion of an eye 22, determine the laser energy of a laser beam according to the optical density measurement, and instruct a laser device to direct the laser beam with the laser energy through the outer portion of the eye 22 to the target portion of the eye 22.

In the example, the system 10 includes an image capture system 12, a laser device 15, and a computing system 20. Computing system 20 includes one or more interfaces (IFs) 24, logic 26, and one or more memories 28. Logic 26 includes a control computer 30 and computer code such as a densitometry module 36, a laser energy module 38, and a laser control program 34. Memories 28 store the computer code, image data 40, and a data structure such as a table 42.

The eye 22 may be an eye of any suitable living organism, such as a human. The eye 22 may comprise different portions. In certain embodiments, a laser beam may be directed towards a target portion in order to photodisrupt the tissue of the target portion. The laser beam may pass through an outer portion of the eye 22 to reach the target portion. The outer portion is typically an anterior portion with respect to the target portion. A portion may refer to any suitable portion of the eye 22. In certain embodiments, a portion may refer to a layer of the cornea. Corneal layers, from anterior to posterior, include the epithelium, Bowman's layer, stroma, Descemet's membrane, and endothelium. For example, the outer portion may be an outer layer of a cornea, and the target portion may be an inner layer of the cornea. In certain embodiments, a portion may refer to a part of the eye. Parts of the eye, from anterior to posterior, include the cornea, aqueous humor, lens, vitreous humor, and retina. For example, the outer portion may be the cornea and aqueous humor, and the target portion may be the crystalline lens.

The image capture system 12 captures an image of the eye 22 from which measurements of optical density of the eye 22 may be calculated. In certain embodiments, the image capture system 12 may utilize a slit-scan method, which may guide light in a linear and/or rotated manner. For example, the image capture system 12 may be a Scheimpflug image capture system such as a Scheimpflug slit camera. In certain embodiments, the image capture system 12' may utilize a Scheimpflug technique combined with a Placido technique that generates an image from concentric rings reflected from the eye 22. In certain embodiments, the image capture system 12 may be an optical coherence tomography (OCT) system that uses low coherence interferometry to capture an image of the eye 22.

The image data 40 records the image of the eye 22. The image data 40 may have one or more values for each pixel of the image. Each pixel corresponds to a location of the eye, and the values indicate the optical density at the location. Examples of images are described in more detail with reference to FIG. 2.

The densitometry module 36 determines an optical density measurement of the outer portion from the image data 40. The optical density measurement may include one or more optical density values for one or more locations of the outer portion of the eye. Each optical density value indicates an optical density at a particular location of the outer portion of the eye.

The optical density measurement may be determined from the image data 40 in any suitable manner. In certain embodiments, the pixel value at a pixel may be used to determine the optical density value for the location corresponding to the pixel. A calibration table may map pixel values to optical density values indicated by the pixel values. For example, a calibration table may map pixel intensity values (0 to 255) to standardized optical density units (ODU) indicated by the intensity values.

The laser energy module 38 determines the laser pulse energy according to the optical density measurement. In certain embodiments, the laser energy module 38 determines the laser energy by accessing a data structure (such as the table 42) that maps optical density values to corresponding laser energy adjustment values. A laser energy adjustment value that corresponds to an optical density value may be an adjustment that can be made to the laser energy in order to compensate for optical density indicated by the optical density value. For example, an adjustment value of X joules (J) that corresponds to Y optical density units (ODU) indicates that the laser energy should be increased by XJ to compensate for optical density of Y ODU. X and Y can have any suitable values. In certain examples, more optical density may require a larger increase in laser energy, and less optical density may require a little or no increase in laser energy. The mappings may be determined from experimental data. The laser energy module 38 may identify the appropriate adjustment value and then adjust the laser energy using the adjustment value.

The laser energy module 38 can use any suitable manner to determine an initial energy (that can be later adjusted). In certain embodiments, the laser energy module 38 determines the initial laser energy according to a corneal depth. For example, a table that maps corneal depth and laser energy may be used to determine the initial laser energy. Then, the initial laser energy can be adjusted according to the laser energy adjustment value that compensates for optical density.

In certain embodiments, the laser energy module 38 determines the laser energy according to a laser energy formula. In the embodiments, the laser energy formula may be a mathematical function with one or more variables, e.g., an optical density value and other variables such as a corneal depth and/or a patient parameter. For example, an optical density value and a corneal depth for a location may be input into the function to yield a laser energy value for that location.

The laser module 38 sends the laser energy that it calculated to the laser control program 34. The laser control program 34 instructs controllable components of the laser device 15 to direct the laser beam with the laser energy through the outer portion to the target portion of the eye 22. In certain embodiments, the laser device 15 can generate pulsed laser radiation (such as a laser beam) with the laser energy and ultrashort pulses (such as pico-, femto-, or attosecond pulses). The laser device 15 can direct the pulsed laser beam through an outer portion of an eye 22 to a target portion of the eye 22 to photodisrupt tissue of the target portion.

Figure 1B:
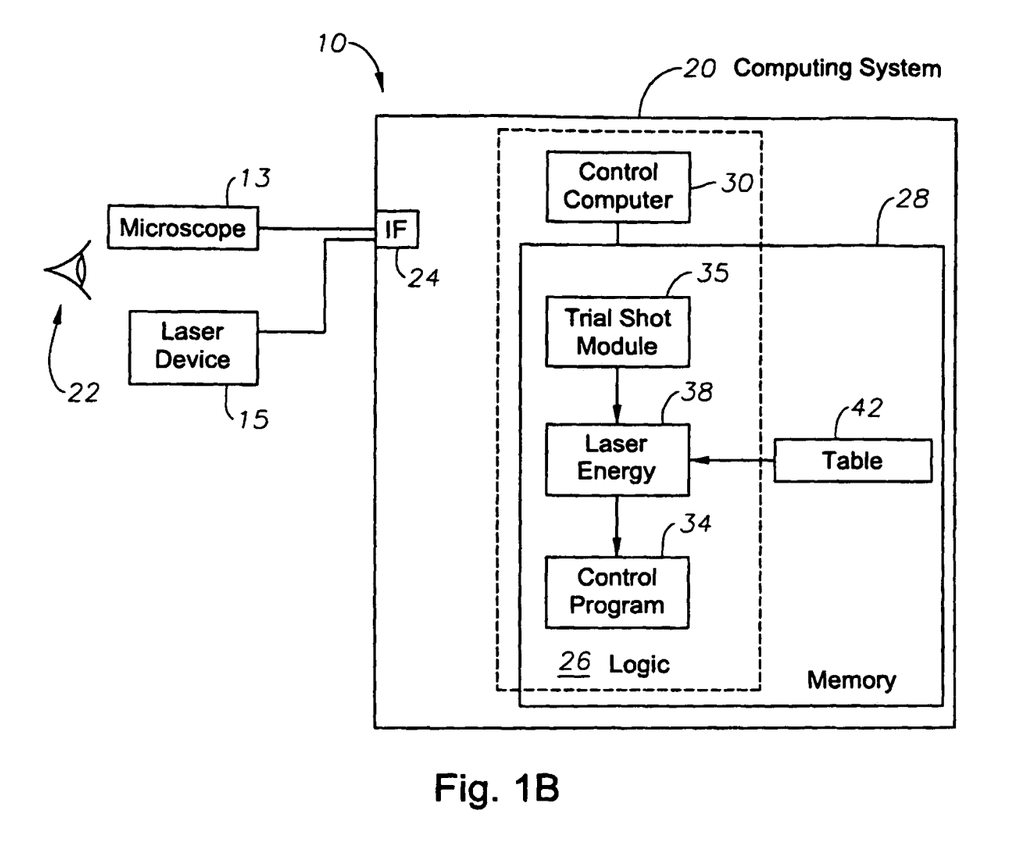
FIG. 1B illustrates an example of a system that can adjust laser energy according to trial shots in certain embodiments.

FIG. 1B illustrates an example of a system 10 that can adjust laser energy according to trial shots in certain embodiments. In certain embodiments, the system 10 can instruct the laser device to direct trial shots towards a trial portion, establish effects of the trial shots on the trial portion, determine the laser energy according to the effects, and instruct the laser device to direct the laser beam with the laser energy towards the target portion of the eye 22.

In the illustrated example, system 10 includes a microscope 13 in place of (or in addition to) the image capture system 12 and a trial shot module 35 in place of (or in addition to) the densitometry module 36. The microscope 13 can be any suitable microscope capable of viewing the eye 22 and may be used to determine the effect of a trial shot on the cornea of the eye 22.

The trial shot module 35 can instruct the laser device to direct trial shots towards a trial portion. A trial shot may be a laser pulse directed towards a trial portion to determine laser energy. A trial portion may be an inessential portion of tissue, such as tissue that is removed from (and may be discarded from) a patient cornea or donor cornea. A trial shot may be associated with parameters such as the laser energy of the shot, corneal depth of the shot (which may be measured in the z-direction as described below), or size and shape of the shot. The parameters may have any suitable values. For example, the shot may be rounded or angular. The trial shot module 35 can direct the trial shots in any suitable pattern of any suitable size and shape. Examples of how trial shots may be directed are described below.

Figure 2A:
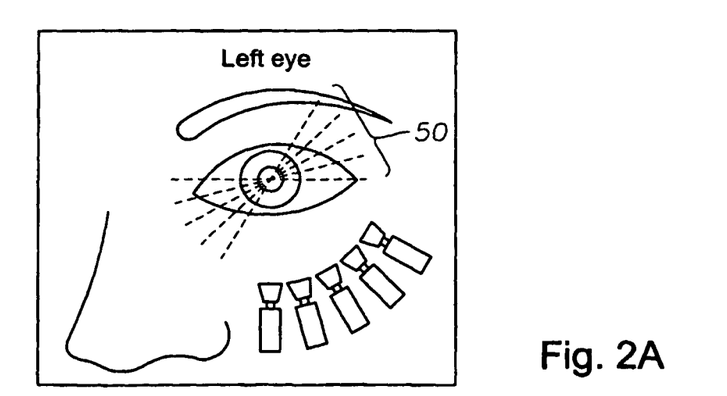
FIGS. 2A through 2C illustrate examples of the operation of an image capture system according to certain embodiments.
Figure 2B:
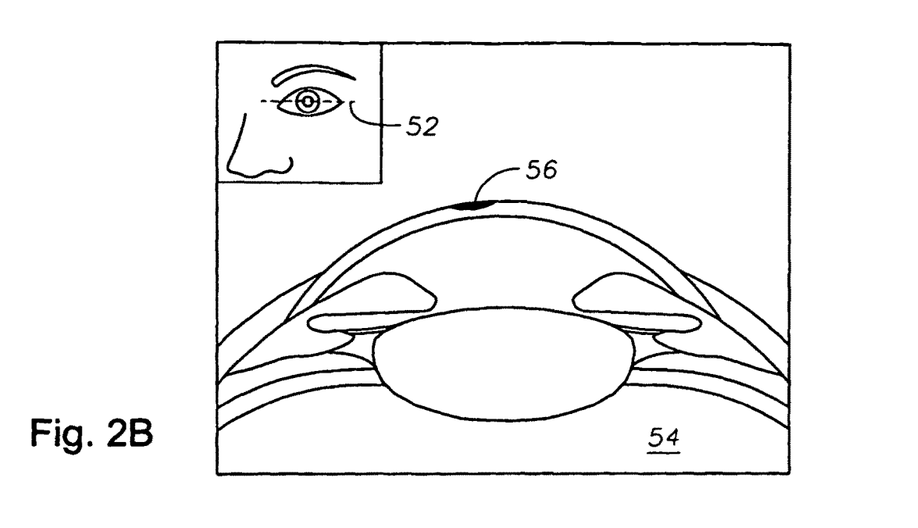
Figure 2C:
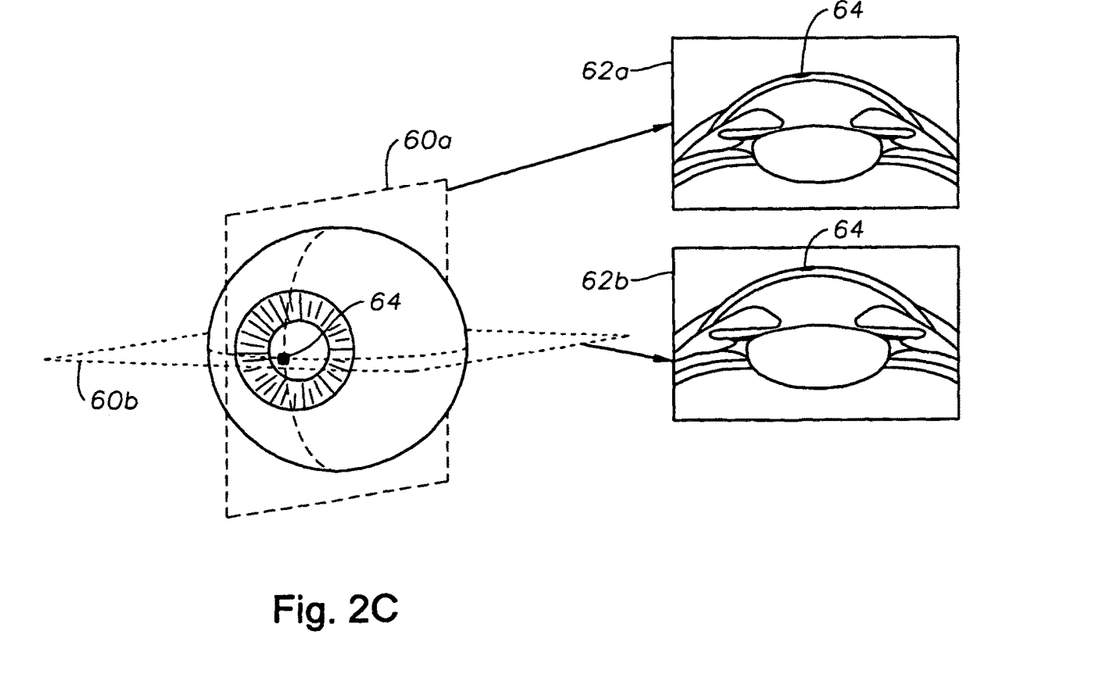
Figure 3A:
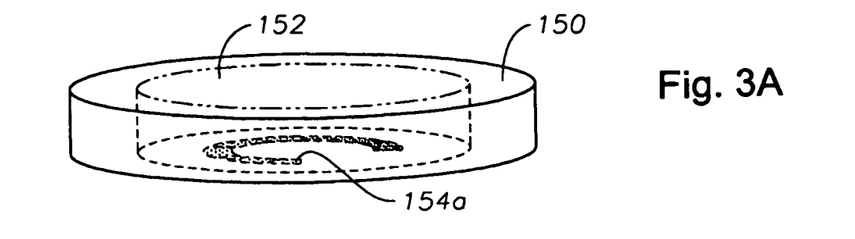
Figure 3B:
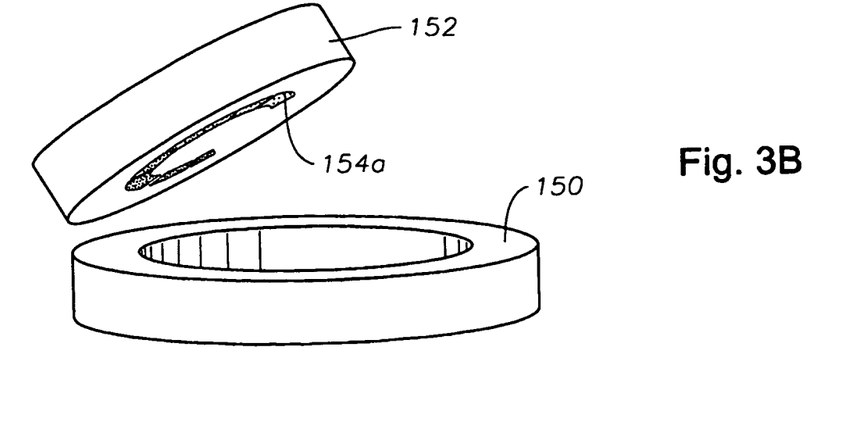
Figure 3C:
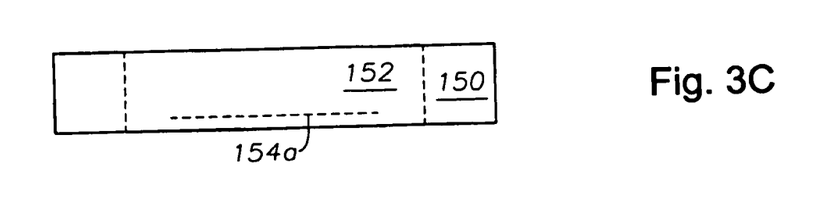
Figure 3D:
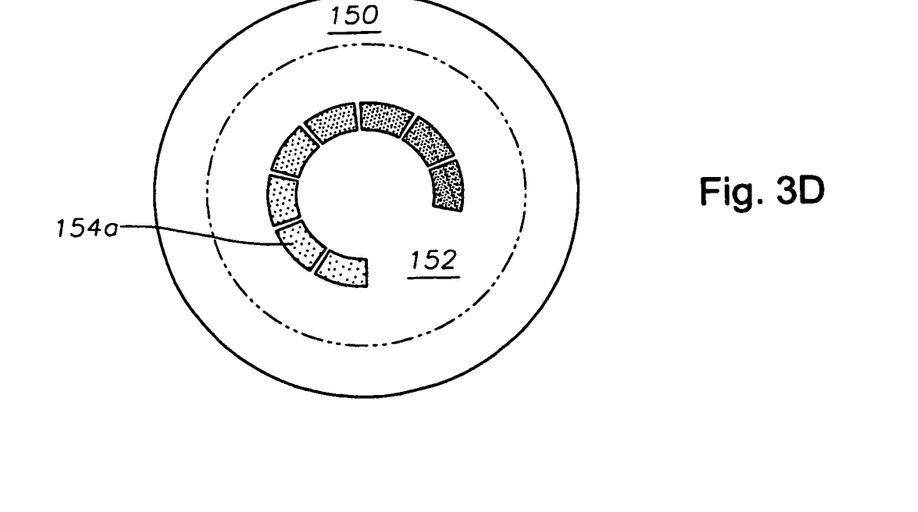
Figure 4A:
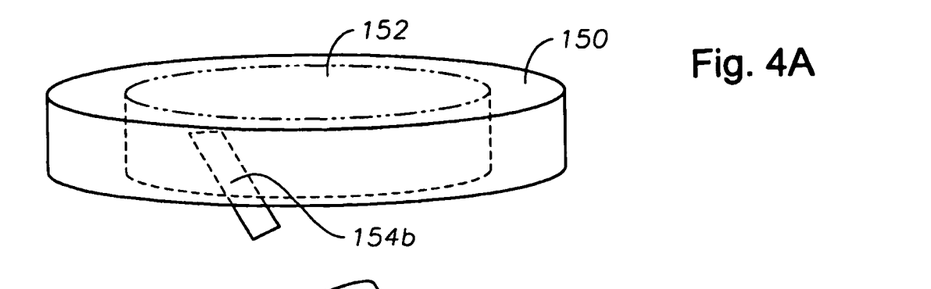
Figure 4B:
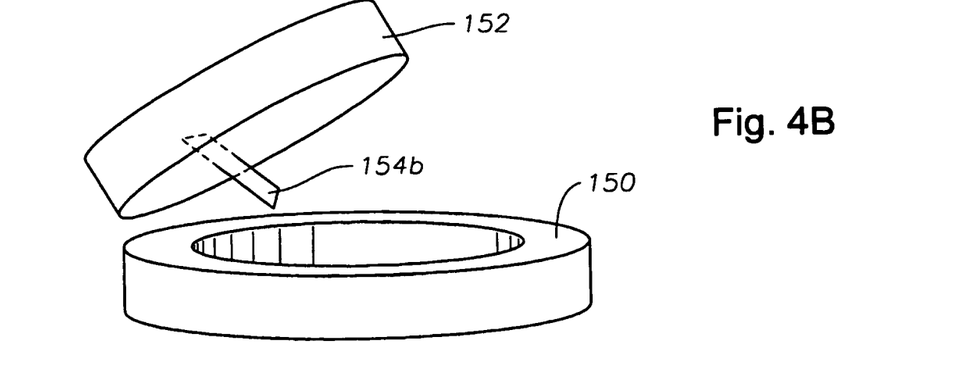
Figure 4C:
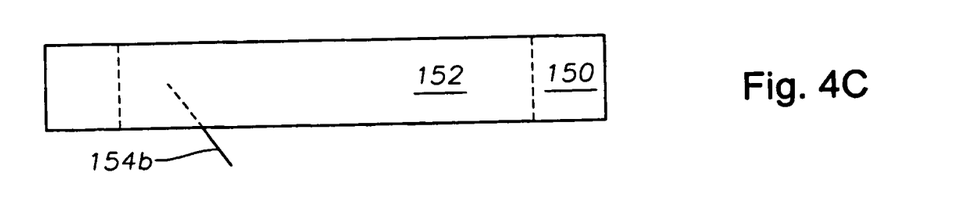
Figure 4D:
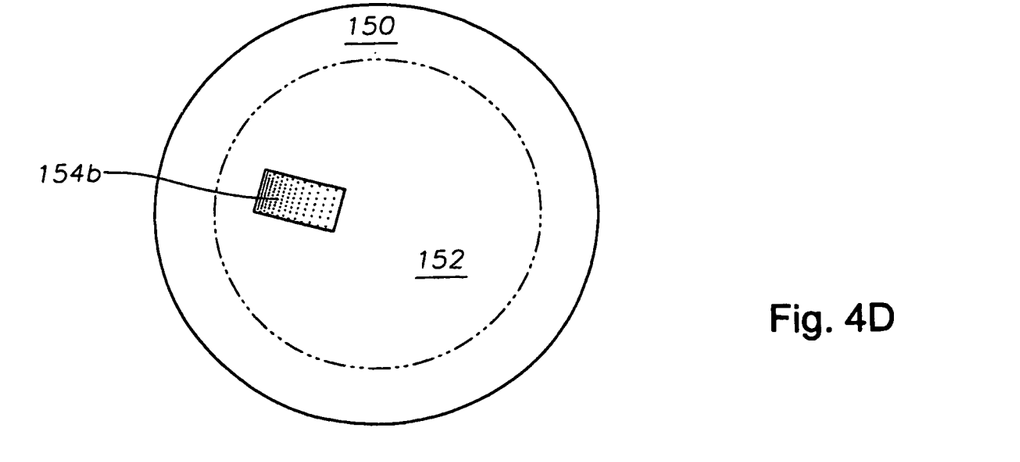

FIGS. 2A through 2C illustrate examples of the operation of an image capture system according to certain embodiments. FIG. 2A illustrates an example of the edges of planes 50 of an eye that can be imaged by an image capture system. FIG. 2B illustrates an example of a particular plane 52 and an image 54 generated of the plane 52. Image 54 shows cloudiness 56 of the cornea. FIG. 2C illustrates an example of images that may be generated by an image capture system. The image capture system may generate images 62 (*a-b*) of planes 60 (*a-b*) of an eye. For example, image 62*a* is of plane 60*a*, and image 62*b* is of plane 60*b*. Images 62 show cloudiness 64 of the cornea.

FIGS. 3A through 4D illustrate examples of directing trial shots at a patient cornea according to certain embodiments. In the examples, a patient cornea 150 has inessential tissue 152, such as a diseased portion that is to be removed and may be replaced with a donor cornea. The inessential tissue 152 serves as a trial portion for trial shots 154.

FIGS. 3A through 3D illustrate an example of directing a pattern of trial shots 154a at a patient cornea according to certain embodiments. In the example, each trial shot 154a of the pattern has a different laser energy. For example, a first trial shot has a first laser energy and a second trial shot has a second laser energy different from the first laser energy. In the example, the trial shots 154a of the pattern may each be directed to the same corneal depth, that is, the trial shots 154a may lay on the same corneal plane.

FIGS. 4A through 4D illustrate another example of directing a pattern of trial shots 154b at a patient cornea according to certain embodiments. In the example, each trial shot 154b of the pattern has a different corneal depth such that the pattern lies at an angle (greater than zero) to a corneal plane at a constant corneal depth. For example, a first trial shot has a first corneal depth and a second trial shot has a second corneal depth different from the first corneal depth. In the example, the trial shots 154b of the pattern may each have the same laser energy. In another example, the energy level of the second trial shot may differ from the energy level of the first trial shot to determine the endothelium level with the required energy.

Figure 5A:
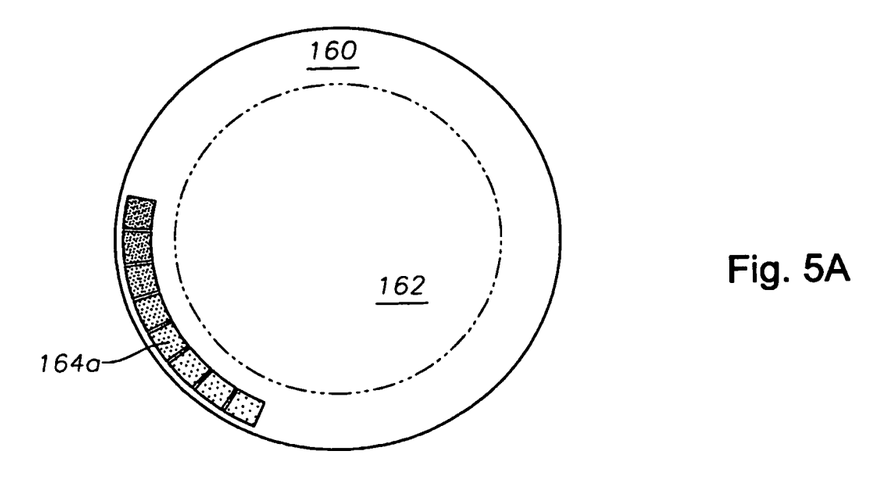
FIGS. 5A and 5B illustrate examples of directing trial shots at a donor cornea according to certain embodiments.
Figure 5B:
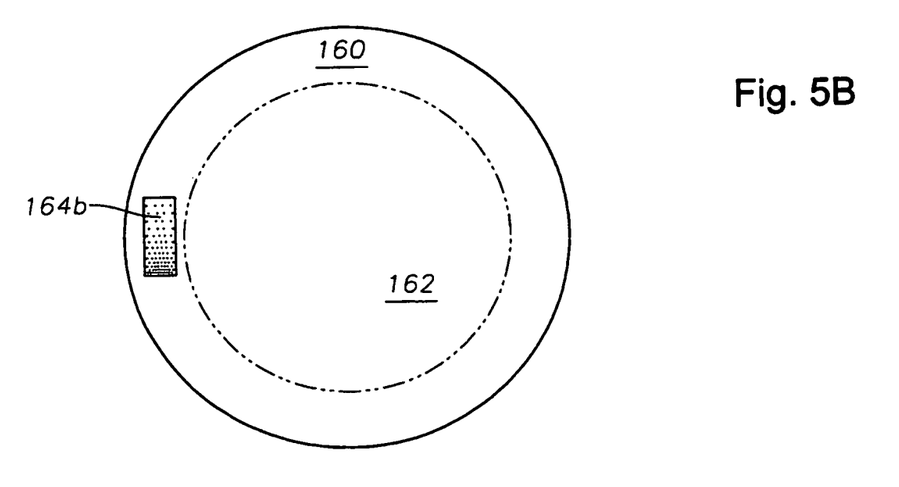

FIGS. 5A and 5B illustrate examples of directing trial shots at a donor cornea according to certain embodiments. In the examples, a donor cornea 160 has inessential tissue 162, such as an excess portion that is to be removed from the portion of the donor cornea 160 to be implanted in a patient. The inessential tissue 162 serves as a trial portion for trial shots 164.

FIG. 5A illustrates an example of directing trial shots at a donor cornea in a manner similar to that of FIGS. 3A through 3D. In the example, each trial shot 164a of the pattern has a different laser energy, and may each be directed to the same corneal depth.

FIG. 5B illustrates an example of directing trial shots at a donor cornea in a manner similar to that of FIGS. 4A through 4D. In the example, each trial shot 164b of the pattern has a different corneal depth such that the pattern lies at an angle (greater than zero) to a corneal plane of a constant corneal depth. Each trial shot 164b may have the same laser energy. In another example, the energy level of the second trial shot may differ from the energy level of the first trial shot to determine the endothelium level with the required energy.

Figure 6:
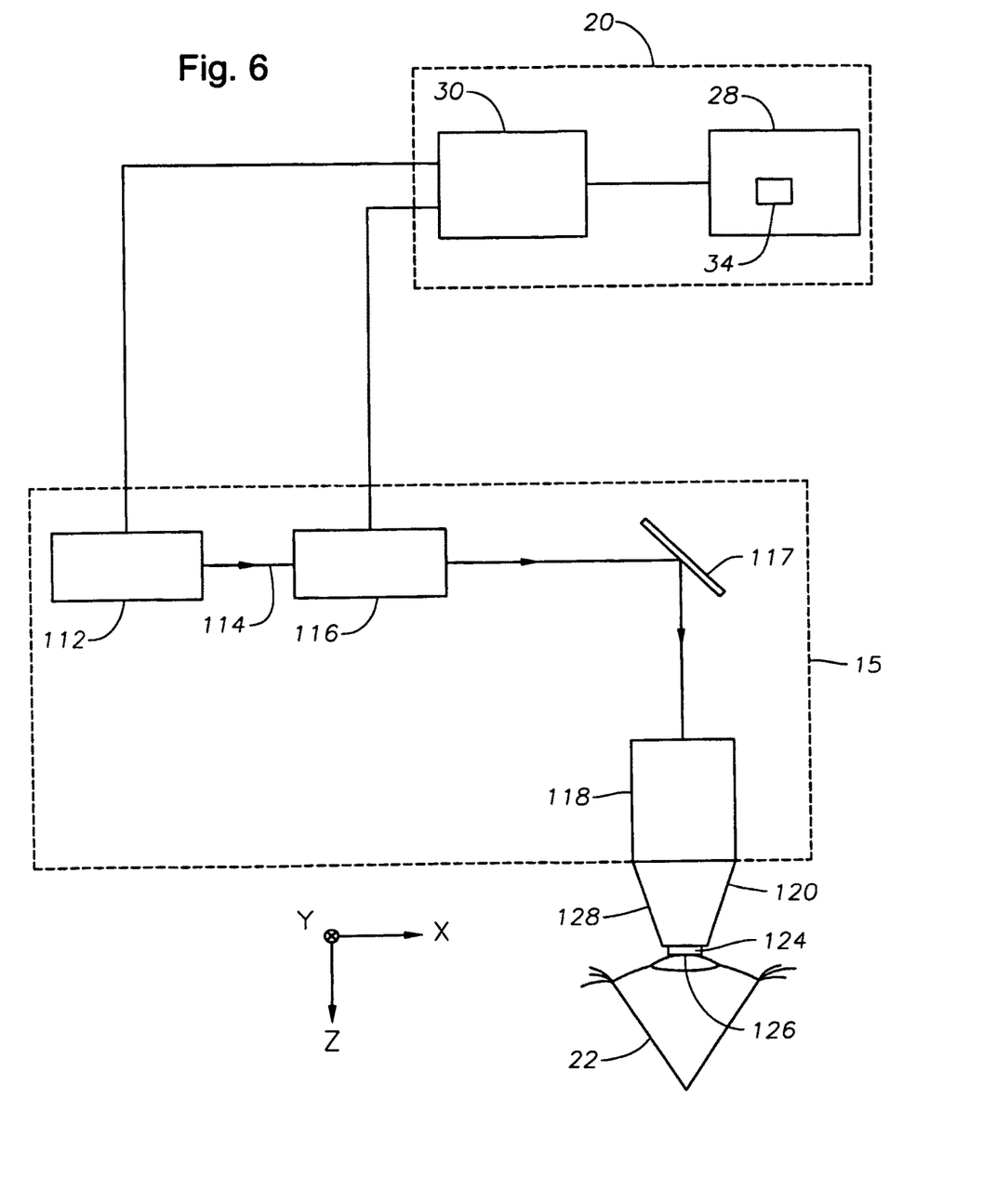
FIG. 6 illustrates an example of a laser device and a control computer configured to photodisrupt tissue according to certain embodiments.

FIG. 6 illustrates an example of a laser device 15 and a control computer 30 configured to photodisrupt tissue according to certain embodiments. In the embodiments, the laser device 15 can generate pulsed laser radiation with the calculated laser energy and ultrashort pulses (such as pico-, femto-, or attosecond pulses). The laser device 15 can direct the pulsed laser beam through an outer portion of an eye to a target portion of the eye to photodisrupt tissue of the target portion. The control computer 30 can receive an optical density measurement of the outer portion, determine the laser energy according to the optical density measurement, and instruct the one or more controllable components to direct the laser beam with the laser energy through the outer portion to the target portion.

In certain embodiments, the laser beam may form a corneal element (such as a corneal flap or corneal cap), which may be removed to allow an excimer laser to apply a refractive correction. The corneal element may or may not be replaced after the refractive correction. In certain embodiments, the laser beam may form a lenticule (or lenticle) that may be removed to yield a refractive correction.

In the illustrated example, the computing system 20 includes a control computer 30 and a memory 28. The memory 28 stores a control program 34. The laser device 15 includes a laser source 112, a scanner 116, one or more optical elements 117, and/or a focusing objective 118 coupled as shown. The laser device 15 is coupled to a patient adapter 120. The patient adapter 120 includes a contact element 124 (which has an abutment face 126 disposed outwardly from a sample) and a sleeve 128 coupled as shown.

The laser source 112 generates a laser beam 114 with ultrashort pulses. In this document, an "ultrashort" pulse of light refers to a light pulse that has a duration that is less than a nanosecond, such as on the order of a picosecond, femtosecond, or attosecond. The focal point of the laser beam 114 may create a laser-induced optical breakdown (LIOB) in tissues such as the cornea. The laser beam 114 may be precisely focused to allow for precise incisions in the epithelial cell layers, which may reduce or avoid unnecessary destruction of other tissue.

Examples of laser source 112 include femtosecond, picosecond, and attosecond lasers. The laser beam 114 may have any suitable vacuum wavelength, such as a wavelength in the range of 300 to 1500 nanometers (nm), for example, a wavelength in the range of 300 to 650, 650 to 1050, 1050 to 1250, or 1100 to 1500 nm. The laser beam 114 may also have a relatively small focus volume, e.g., 5 micrometers ($\mu$m) or less in diameter. In certain embodiments, the laser source 112 and/or delivery channel may be in a vacuum or near vacuum.

The scanner 116, optical elements 117, and focusing objective 118 are in the beam path. The scanner 116 transversely and longitudinally controls the focal point of the laser beam 114. "Transverse" refers to a direction at right angles to the direction of propagation of the laser beam 114, and "longitudinal" refers to the direction of beam propagation. The transverse plane may be designated as the x-y plane, and the longitudinal direction may be designated as the z-direction. In certain embodiments, the abutment face 126 of the patient interface 120 is on an x-y plane.

The scanner 116 may transversely direct the laser beam 114 in any suitable manner. For example, the scanner 116 may include a pair of galvanometrically actuated scanner mirrors that can be tilted about mutually perpendicular axes. As another example, the scanner 116 may include an electro-optical crystal that can electro-optically steer the laser beam 114. The scanner 116 may longitudinally direct the laser beam 114 in any suitable manner. For example, the scanner 116 may include a longitudinally adjustable lens, a lens of variable refractive power, or a deformable mirror that can control the z-position of the beam focus. The focus control components of the scanner 116 may be arranged in any suitable manner along the beam path, e.g., in the same or different modular units.

One (or more) optical elements 117 direct the laser beam 114 towards the focusing objective 118. An optical element 117 may be any suitable optical element that can reflect and/or refract/diffract the laser beam 114. For example, an optical element 117 may be an immovable deviating mirror. The focusing objective 118 focuses the laser beam 114 onto the patient adapter 120, and may be separably coupled to the patient adapter 120. The focusing objective 118 may be any suitable optical element, such as an f-theta objective.

Patient adapter 120 interfaces with the cornea of the eye 22. In the example, the patient adapter 120 has a sleeve 128 coupled to a contact element 124. The sleeve 128 couples to the focusing objective 118. The contact element 124 is transparent to the laser beam and has an abutment face 126 that interfaces with the cornea and may level a portion of the cornea. In certain embodiments, the abutment face 126 is planar and forms a planar area on the cornea. The abutment face 126 may be on an x-y plane, so the planar area is also on an x-y plane. In other embodiments, the cornea need not have planar area.

The control computer 30 controls controllable components, e.g., the laser source 112 and scanner 116, in accordance with the control program 34. The control program 34 contains computer code that instructs the controllable components of the laser device 15 to focus the pulsed laser beam with a laser energy calculated according to optical density of an outer portion of the eye 22.

In certain examples of operation, the scanner 116 may direct the laser beam 114 to form incisions of any suitable geometry. Examples of types of incisions include bed incisions and lateral incisions. A bed incision is two-dimensional incision that is typically on an x-y plane. The scanner 116 may form a bed incision by focusing the laser beam 114 at a constant z-value under the abutment face 126 and moving the focus in a pattern in an x-y plane. A lateral incision is an incision that extends from under the corneal surface (such as from a bed incision) to the surface. The scanner 116 may form a lateral incision by changing the z-value of the focus of the laser beam 114 and optionally changing the x and/or y values.

Figure 7:
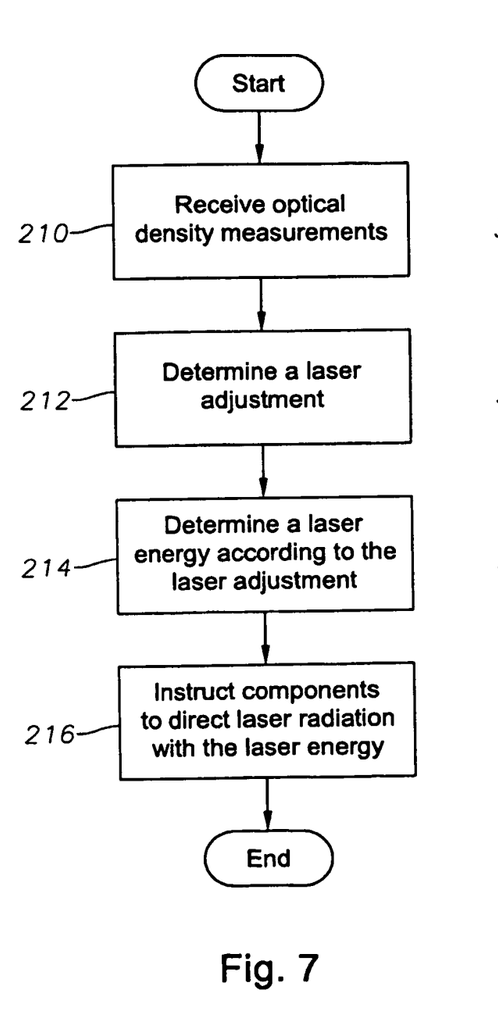
FIG. 7 illustrates an example of a method for adjusting laser energy according to an optical density measurement in certain embodiments.

FIG. 7 illustrates an example of a method for adjusting laser energy according to an optical density measurement in certain embodiments. The method may be performed by a computing system 20. The method begins at step 210, where the computing system 20 receives an optical density measurement of the outer portion of an eye 22. In certain embodiments, the outer portion may be an outer layer of the cornea. In certain embodiments, the optical density measurement may include one or more optical density values for one or more locations of the outer portion, where each optical density value indicates the optical density at a location.

A laser adjustment value is determined according to the optical density measurement at step 212. In certain embodiments, the laser energy module 38 determines the laser adjustment value. In the embodiments, the laser energy module 38 may access a data structure (such as table 42) that associates a number of optical density values with a number of a laser adjustment values. The laser energy module 38 may identify the laser adjustment value for a location associated with the optical density value at the location.

Laser energy is determined according to the laser adjustment value at step 214. In certain embodiments, the laser energy module 38 may determine the laser energy. In the embodiments, the laser energy module may determine an initial laser energy at a location, and then adjust the initial laser energy according to the laser adjustment value for the location.

The laser device 15 is instructed to direct the laser beam with the laser energy through the outer portion to the target portion at step 216. For example, the laser energy module 38 may send instructions to laser device 15 to direct a laser beam at a location with the adjusted laser energy determined for the location.

Figure 8:
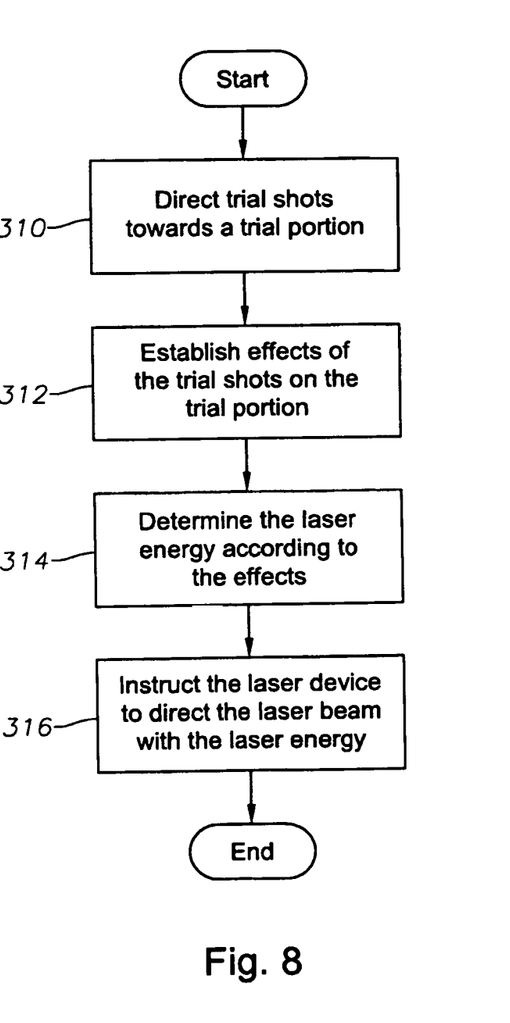
FIG. 8 illustrates an example of a method for adjusting laser energy according to trial shots in certain embodiments.

FIG. 8 illustrates an example of a method for adjusting laser energy according to trial shots in certain embodiments. The method may be performed by a computing system 20. The method begins at step 310, where the computing system 20 instructs a laser device to direct trial shots towards a trial portion. In certain embodiments, the trial portion may be inessential tissue of a donor or patient.

Effects of the trial shots are established at step 312. In certain embodiments, a microscope 13 may be used to identify a trial shot with a satisfactory effect. A satisfactory effect may be one of one or more effects that satisfy one or more requirements (such as the best effect). For example, a satisfactory effect of a trial shot may be creating a cut in the tissue without damaging the tissue.

Laser energy is determined according to the effects at step 314. In certain embodiments, the laser energy module 38 may determine the laser energy. In the embodiments, the laser energy module 38 may identify a trial shot with a satisfactory effect and determine the laser energy to be that of the identified trial shot. In certain embodiments, the laser energy module 38 may be able to interpolate and/or extrapolate the laser energy from the measured effects. For example, if one shot with a lower laser energy did not create a cut, but the next shot with a higher laser energy caused too much damage, a laser energy module between the higher and lower energies may be used.

The laser device 15 is instructed to direct the laser beam with the laser energy to a target portion at step 316. For example, the laser energy module 38 may send instructions to laser device 15 to direct a laser beam towards the target portion with the laser energy.

A component of the systems and apparatuses disclosed herein may include an interface, logic, memory, and/or other suitable element, any of which may include hardware and/or software. An interface can receive input, send output, process the input and/or output, and/or perform other suitable operations. Logic can perform the operations of a component, for example, execute instructions to generate output from input. Logic may be encoded in memory and may perform operations when executed by a computer. Logic may be a processor, such as one or more computers, one or more microprocessors, one or more applications, and/or other logic. A memory can store information and may comprise one or more tangible, computer-readable, and/or computer-executable storage medium. Examples of memory include computer memory (for example, Random Access Memory (RAM) or Read Only Memory (ROM)), mass storage media (for example, a hard disk), removable storage media (for example, a Compact Disk (CD) or a Digital Video Disk (DVD)), database and/or network storage (for example, a server), and/or other computer-readable media.

In particular embodiments, operations of the embodiments may be performed by one or more computer readable media encoded with a computer program, software, computer executable instructions, and/or instructions capable of being executed by a computer. In particular embodiments, the operations may be performed by one or more computer readable media storing, embodied with, and/or encoded with a computer program and/or having a stored and/or an encoded computer program.

Although this disclosure has been described in terms of certain embodiments, modifications (such as changes, substitutions, additions, omissions, and/or other modifications) of the embodiments will be apparent to those skilled in the art. Accordingly, modifications may be made to the embodiments without departing from the scope of the invention. For example, modifications may be made to the systems and apparatuses disclosed herein. The components of the systems and apparatuses may be integrated or separated, and the operations of the systems and apparatuses may be performed by more, fewer, or other components. As another example, modifications may be made to the methods disclosed herein.

The methods may include more, fewer, or other steps, and the steps may be performed in any suitable order.

Other modifications are possible without departing from the scope of the invention. For example, the description illustrates embodiments in particular practical applications, yet other applications will be apparent to those skilled in the art. In addition, future developments will occur in the arts discussed herein, and the disclosed systems, apparatuses, and methods will be utilized with such future developments.

The scope of the invention should not be determined with reference to the description. In accordance with patent statutes, the description explains and illustrates the principles and modes of operation of the invention using exemplary embodiments. The description enables others skilled in the art to utilize the systems, apparatuses, and methods in various embodiments and with various modifications, but should not be used to determine the scope of the invention.

The scope of the invention should be determined with reference to the claims and the full scope of equivalents to which the claims are entitled. All claims terms should be given their broadest reasonable constructions and their ordinary meanings as understood by those skilled in the art, unless an explicit indication to the contrary is made herein. For example, use of the singular articles such as "a," "the," etc. should be read to recite one or more of the indicated elements, unless a claim recites an explicit limitation to the contrary. As another example, "each" refers to each member of a set or each member of a subset of a set, where a set may include zero, one, or more than one element. In sum, the invention is capable of modification, and the scope of the invention should be determined, not with reference to the description, but with reference to the claims and their full scope of equivalents.

What is claimed is:

1. A device comprising:
    a laser device configured to direct a laser beam with a laser energy and ultrashort pulses towards a target portion of an eye; and
    a control computer configured to:
        instruct the laser device to direct a plurality of trial shots towards a trial portion of a cornea to photodisrupt tissue of the target portion under a surface of the cornea, each trial shot located at a different position and depth under the surface of the cornea to create a planar pattern that lies at an angle to a corneal plane at a constant corneal depth, at least one trial shot photodisrupting tissue to create a cut in the cornea without otherwise damaging the surrounding corneal tissue;
        establish a plurality of effects of the trial shots on the trial portion of the cornea using an optical density measurement in the form of a pixel intensity value of the trial portion, the optical density measurement comprising one or more optical density values in one or more locations of the cornea, each optical density value indicating an optical density for a location of the cornea;
        identify the trial shot that photodisrupts tissue to create a cut in the cornea without otherwise damaging the surrounding corneal tissue;
        determine the laser energy according to the identified trial shot and further based on the optical density value and a corneal depth for the location; and
        instruct the laser device to direct the laser beam with the laser energy towards the target portion of the eye.

2. The device of claim 1, the control computer further configured to:
    direct a plurality of next trial shots towards the trial portion, each next trial shot located at a different position and the same depth to create a next planar pattern that lies parallel to the corneal plane at the constant corneal depth, the next trial shots comprising a first trial shot with a first laser energy and a second trial shot with a second laser energy different from the first laser energy.

3. The device of claim 1, the control computer further configured to:
    direct a plurality of next trial shots towards the trial portion, each next trial shot located at a different position and the same depth to create a next planar pattern that lies parallel to the corneal plane at the constant corneal depth.

4. The device of claim 1, the trial portion comprising inessential tissue.

5. The device of claim 1, the trial portion comprising inessential donor tissue.

6. The device of claim 1, the trial portion comprising inessential patient tissue.

* * * * *